United States Patent [19]

Sonnenberg et al.

[11] Patent Number: 5,223,118
[45] Date of Patent: Jun. 29, 1993

[54] METHOD FOR ANALYZING ORGANIC ADDITIVES IN AN ELECTROPLATING BATH

[75] Inventors: Wade Sonnenberg, Foxboro; Roger Bernards, Wellesley; Patrick Houle, Framingham; Gordon Fisher, Sudbury, all of Mass.

[73] Assignee: Shipley Company Inc., Newton, Mass.

[21] Appl. No.: 666,798

[22] Filed: Mar. 8, 1991

[51] Int. Cl.$^5$ .................. G01N 27/416; C25D 21/14
[52] U.S. Cl. .................................. 205/81; 204/153.1; 427/10
[58] Field of Search ............... 205/81; 204/153.1, 434; 427/8, 10

[56] References Cited

U.S. PATENT DOCUMENTS

| | | | |
|---|---|---|---|
| 3,925,168 | 12/1975 | Costas | 204/153.1 |
| 4,132,605 | 1/1979 | Tench et al. | 204/1 T |
| 4,146,437 | 3/1979 | O'Keefe | 204/153.1 |
| 4,324,621 | 4/1982 | Kerby | 204/153.1 |
| 4,443,301 | 4/1984 | Kerby | 204/153.1 |
| 4,631,116 | 12/1986 | Ludwig | 204/153.1 |
| 4,725,339 | 2/1988 | Bindra | 204/153.1 |
| 4,897,165 | 1/1990 | Bernards et al. | 204/24 |
| 4,917,774 | 4/1990 | Fisher | 204/153.1 |

OTHER PUBLICATIONS

Tench et al., Pulse Voltommetric Stripping Analysis of Acid Copper Plating Baths, *J. Electrochem, Soc.*, Apr. 1985, pp. 831–834.

Primary Examiner—John Niebling
Assistant Examiner—William T. Leader
Attorney, Agent, or Firm—Robert L. Goldberg

[57] ABSTRACT

A direct method of analyzing brighteners and levelers used in metal electroplating baths. The method is based on the differential adsorption of these additives on a working electrode during a sequence of steps prior to and during metal plating. The sensitivity of the method allows for the determination of both brightener and leveler in the same sample without cyclic processing.

19 Claims, 9 Drawing Sheets

METHOD FOR ANALYZING ORGANIC ADDITIVES IN AN ELECTROPLATING BATH

BACKGROUND OF THE INVENTION

I. Introduction

This invention relates to electrolytic plating and more particularly, to a method of analyzing organic additives in an electroplating bath.

II. Discussion of Related Art

Electroplating is a complex process involving multiple ingredients in a plating bath. It is important that the concentration of several of the ingredients be kept within close tolerances in order to obtain a high quality deposit. In some cases, chemical analysis of individual solution constituents can be made regularly (such as pH measurement for acid content), and additions made as required. However, other addition agents such as brighteners, leveling agents, suppressants, etc., together with impurities, cannot be individually analyzed on an economical or timely basis by a commercial plating shop. Their operating concentration is low and their quantitative analysis is complicated and subject to error.

A prior art method for controlling such ingredients in an electroplating bath is to make regular additions of particular ingredients based upon empirical rules established by experience. However, depletion of particular ingredients is not always constant with time or with bath use. Consequently, the concentration of the ingredients is not actually known and the level in the bath eventually diminishes or increases to a level where it is out of the acceptable range tolerance. If the additive content goes too far out of range, the quality of the metal deposit suffers and the deposit may be dull in appearance and/or brittle or powdery in structure. Other possible consequences include low throwing power and/or plating folds with bad leveling.

Another prior art method for plating bath control is to plate articles or samples and visually evaluate the plating quality to determine if the bath is performing satisfactorily. In standard Hull Cell and "Bone Pattern" tests, a specially shaped test specimen is plated and then evaluated to determine the quality of the deposit along with shape. This is a time consuming test which gives at best a rough approximation of the concentration of the constituents of the bath.

The electroplating of through-hole interconnections in the manufacture of multilayer printed circuit boards is an example of the use of an electroplating metal where high quality plating is required. It is known that the concentration of the organic additives, such as brighteners and levelers, within the plating solution must be maintained in low concentration (typically less than 100 parts per million parts of solution - ppm) in order to obtain acceptable deposits on printed circuit boards. This must be done to maintain proper mechanical properties for resistance to thermal stresses encountered during manufacture and use and to assure the proper thickness of the deposit in the through-holes and leveling. The concentration of the organic additive agents fluctuates because of oxidation at the anode, reduction at the cathode, and chemical degradation. When the additive level is insufficient, deposits are burned and powdery in appearance whereas excessive addition agents induce brittleness and non-uniform deposition. Hull cell tests, Bone Pattern tests, and Pencil tests, combined with periodic additions of fresh additives, were the methods used to maintain a control concentration of the additive until recently. These methods were unreliable and circuit board quality suffered as a consequence of these unreliable methods.

A more recent method for evaluating the quality of an electroplating bath was disclosed in Tench U.S. Pat. No. 4,132,605 (hereafter the Tench patent). In accordance with the procedures of the Tench patent, the potential of a working electrode is swept through a voltammetric cycle, including a metal plating range and a metal stripping range, for at least two baths of known plating quality and an additional bath whose quality or concentration of brightener is to be evaluated. The integrated or peak current utilized during the metal stripping range is correlated with the quality of the bath of known quality. The integrated or peak current utilized to strip the metal in the bath of unknown quality is compared to the correlation and its quality evaluated. In a preferred embodiment of said patent, the potential of an inert working electrode is swept by a function generator through the voltammetric cycle. A counter electrode immersed in the plating bath is coupled in series with a function generator and a coulometer to measure the charge from the working electrode during the stripping portion of the cycle.

An improvement to the method disclosed in the Tench patent is described by Tench and White, in the *J. Electrochem. Soc.*, "Electrochemical Science and Technology", April, 1985, pp. 831–834 (hereafter the Tench publication). In accordance with the Tench publication, contaminant buildup in the copper plating bath affects the copper deposition rate and thus interferes with brightener analysis. The Tench publication teaches that rather than continuous sweep cycle utilized in the above-referenced patent, a method be used involving sequentially pulsing the electrode between appropriate metal plating, metal stripping, cleaning, and equilibrium potentials whereby the electrode surface is maintained in a clean and reproducible state. Stated otherwise, where the process of the Tench patent involves a continuous voltammetric sweep between about −600 mV and +1,000 mV versus a working electrode and back over a period of about 1 minute, the Tench publication pulses the potential, for example at −250 mV for 2 seconds to plate, +200 mV for a time sufficient to strip, +1,600 mV to clean for seconds, +425 mV for 5 seconds to equilibrate, all potentials referenced to a saturated Calomel electrode, after which the cycle is repeated until the difference between successive results are within a predetermined value, for example, within 2% of one another.

The procedure of the Tench publication provides some improvement over the procedure of the Tench patent, but during continuous use of an electroplating bath and following successive analysis, contaminants build up on the electrodes and analysis sensitivity is lost.

An improvement over both the Tench patent and the Tench publication is found in U.S. Pat. No. 4,917,774. In accordance with the invention, in order to prevent contaminant buildup on the electrodes, a pause without applied potential is used following each completed cycle. This is effectuated by an open circuit condition or an applied potential equal to or approximately equal to the open circuit potential of the inert electrode in the bath following the cycle of metal plating, metal stripping, and if a pulse system is used, cleaning. An applied potential equal to or approximately equal to the open circuit potential can be applied in lieu of an equilibration step, or an open circuit condition can be used following equilibration. During either this applied potential or the open circuit condition, contaminants are either eliminated from the electrode surface or fail to deposit on the surface. The method involves passing an inert electrode through a predetermined sequence of voltammetric steps including a metal plating step, a metal stripping step, and a conditioning step without applied potential, correlating quantity of brightener with the coulombs utilized during the metal stripping step, and using the same predetermined sequence of voltammetric steps for a bath having an unknown quantity of additive.

All of the prior art methods for evaluating the quality of electroplating baths are based on various voltammetric cycles involving metal plating and stripping. The prior art methods are also cyclic, meaning that the entire process has to be repeated more than once before a final determination of the level of brightener is made. The quantity of metal deposited during the metal plating cycle and subsequently redissolved in the metal stripping cycle, is related to the concentration of brightener affecting the rate of deposition. The methods observe the current density of copper ions reducing on an electrode at a given potential. This can then be related to brightener concentration since brightener will increase the current density. These voltammetric methods may be used to analyze the brightener content, content of organic contamination and the chloride content.

The method of the present invention differs from conventional cycled voltammetric methods. The concentration of leveling agents and brighteners in an electroplating bath induces leveling of the deposit by inhibiting deposition at peaks, where the concentration remains high, and enhancing deposition in recesses, where the concentration becomes depleted as it is diffusion limited. It has been found that the brightness and leveling phenomena is related to diffusion controlled adsorption of these components. In the present invention, the quantity of these additives in the electroplating bath is measured directly.

The use of a direct method of measuring such components is not taught in the prior art and the use of such methods is discouraged. For example, U.S. Pat. No. 4,132,605, col. 3, lines 12-21, states that conventional voltammetric analysis in which the substance to be determined is, itself, adsorbed and then stripped from the electrode surface, is not a suitable method for determining the quantity of low concentration additives in a plating bath because the quantity of the additive cannot be separated from the large quantity of metal being deposited.

SUMMARY OF THE INVENTION

The subject invention is a novel method for determining the quantity of brighteners and levelers present in an electroplating bath. The method allows for the determination of both brightener and leveler in one procedure. The method monitors changes in energy output of the system over time for specific steps in the plating process. During plating, complex organics such as brighteners and levelers are readily adsorbed on an electrode. The binding strength of brighteners to metals is much stronger than that of levelers and this differential strength allows for controlled adsorption of the brightener and leveler in distinct steps. An equilibration step allows adsorption of the brightener for a time necessary to determine concentration of brightener. An optional electroplating pulse step can be used before or after equilibration to increase sensitivity or to shorten equilibration time. After the equilibration step, metal is plated, first to measure brightener concentration, and then the rate of change of energy output from the system is recorded in order to determine leveler concentration. The initial potential recorded is a measure of the brightener concentration. When the energy output is plotted versus time, the slope of the line indicates the ratio of brightener to leveler present in the bath. The sensitivity of this process allows for determination of organic additive concentrations down to 1 part per billion (ppb).

DESCRIPTION OF THE PREFERRED EMBODIMENT

The invention disclosed herein differs from both the cyclic voltammetric stripping (CVS) and the cyclic pulse voltammetric stripping method (CPVS) methods disclosed by Tench, in that the method of the present invention is not based on a cyclic process of plating and stripping of metal from an electrode.

Figure 1:
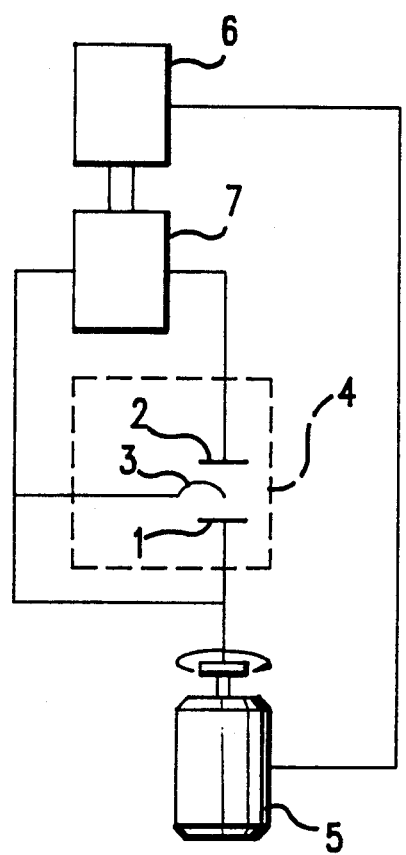
FIG. 1 is a schematic wiring diagram showing a device for practicing the method for the present invention.

FIG. 1 shows the schematic wiring diagram for a device useful in practicing the present invention. Three electrodes, a working electrode (1), a counter electrode (2), and a reference electrode (3), are immersed in a bath cell (4). The counter electrode is selected and designed so as not to be easily polarized in the particular bath being evaluated. This is accomplished in part, by placing the counter electrode close to the working electrode. The working electrode is a suitable metal disk such as platinum, copper, nickel, chromium, zinc, tin, gold, silver, lead, cadmium, solder, glassy carbon, mercury and stainless steel. The working electrode typically has a flat, polished surface, small diameter and may be mounted flush with the end of a Kel-F cylinder. A small diameter disk is preferred since a larger diameter will result in poor sensitivity due to non-uniform current density across the diameter. Other suitable working electrodes include any that provide a uniform current density and controlled agitation. The reference electrode is conventionally, a saturated Calomel reference electrode (SCE). To establish relative motion between the working electrode and the bath, a motor (5) is used to rotate the working electrode to which contact is made by slip brushes.

A computer (6) is used to control an electronic potentiostat (7) which controls the energy input between the working electrode relative to the reference electrode. For laboratory testing of the method, instrumentation such as a Pine Instruments potentiostat under IBM computer control may be used. Using a suitable program, the energy input sequences of the present invention may be applied to the working electrode. The output of the device can also be plotted on an X-Y recorder to graphically display the changes in energy output versus time for each step. The terms "energy input" and "energy output" in the following description of the methods and claims will refer to control of the potential (energy input) while monitoring current density (energy output), or control of current density (energy input) while monitoring potential (energy output).

The following description of the method will be described by reference to energy input as current and energy output as potential, and will be described by reference to standard acid/copper electroplating baths. It is possible however to use the method to control other metal electroplating baths such as nickel, chromium, zinc, tin, gold, silver, lead, cadmium and solder. The working electrode is normally selected or initially plated to match the metal in the plating bath in order to maximize adsorption of the respective brighteners used in the baths.

A typical copper electroplating solution useful for the practice of this invention has a composition as follows:

| | |
|---|---|
| copper ions | 2.5 to 40.0 g/l |
| sulfuric acid | 50 to 450 g/l |
| chloride ions | 20 to 100 mg/l |
| organic additive | as required |
| water | to 1 liter |

The plating solutions are used in the conventional manner, with operating temperatures preferably between 10° C. and 30° C., and controlled solution agitation.

The preferred method of the present invention begins with a cleaning step to clean the working electrode. An anodic cleaning process may be carried out galvanostatically at approximately 80 ASF for a time sufficient to clean the electrode or until the voltage reaches 1.6 volts. Alternatively, the cleaning may be carried out at 1.6 volts for approximately 10 seconds, or the electrode may be cleaned chemically by treating with nitric acid followed by rinsing with deionized water.

The second step is to plate a thin layer of copper, approximately 5–500 microinches, on the disk by placing the disk in an electroplating bath solution for 10–300 seconds at a plating current between 1–100 ASF. The solution may be a standard solution containing only the inorganic chemicals or an actual bath. The use of this thin film of copper eliminates problems associated with nucleation of metal on the disk during analysis. If the disk is made of a metal which readily adsorbs organic additives, or induces potential driven adsorption of the additives, used in electroplating baths, this step is not needed.

In the next step, the bath sample may be substituted for the standard solution containing only the inorganic chemicals, if not used in the initial plating step, with controlled agitation. Brighteners and levelers used in conjunction with the present invention include any sulfonated sulfur-containing compounds which are known and used in the electroplating art. Suitable brighteners useful in the practice of the invention contain the group $S-R_1-S$, where $R_1$ may be an alkyl or aryl group, and are illustrated by the following structural formulas: $HO_3S-R_2-SH$, $HO_3S-R_2-S-S-R_2-SO_3H$ (where $R_2=C_1-C_6$) and $HO_3S-Ar-S-S-Ar-SO_3H$ (where Ar = phenyl or naphthyl). Typical of such compounds are those disclosed in U.S. Pat. Nos. 3,770,598, 4,374,709, 4,376,685, 4,555,315 and 4,673,469, all incorporated herein by reference.

Levelers that may be added to the bath included those which contain a $N-R_1-S$ group, where $R_1$ may be an alkyl or aryl group, and are illustrated by compounds disclosed in U.S. Pat. Nos. 4,376,685, 4,555,315, and 3,770,598, all incorporated herein by reference.

In addition to the organic components identified above, as is known in the art, other organic additives may be used in the plating solution such as surfactants, wetting agents and carriers.

Figure 2:
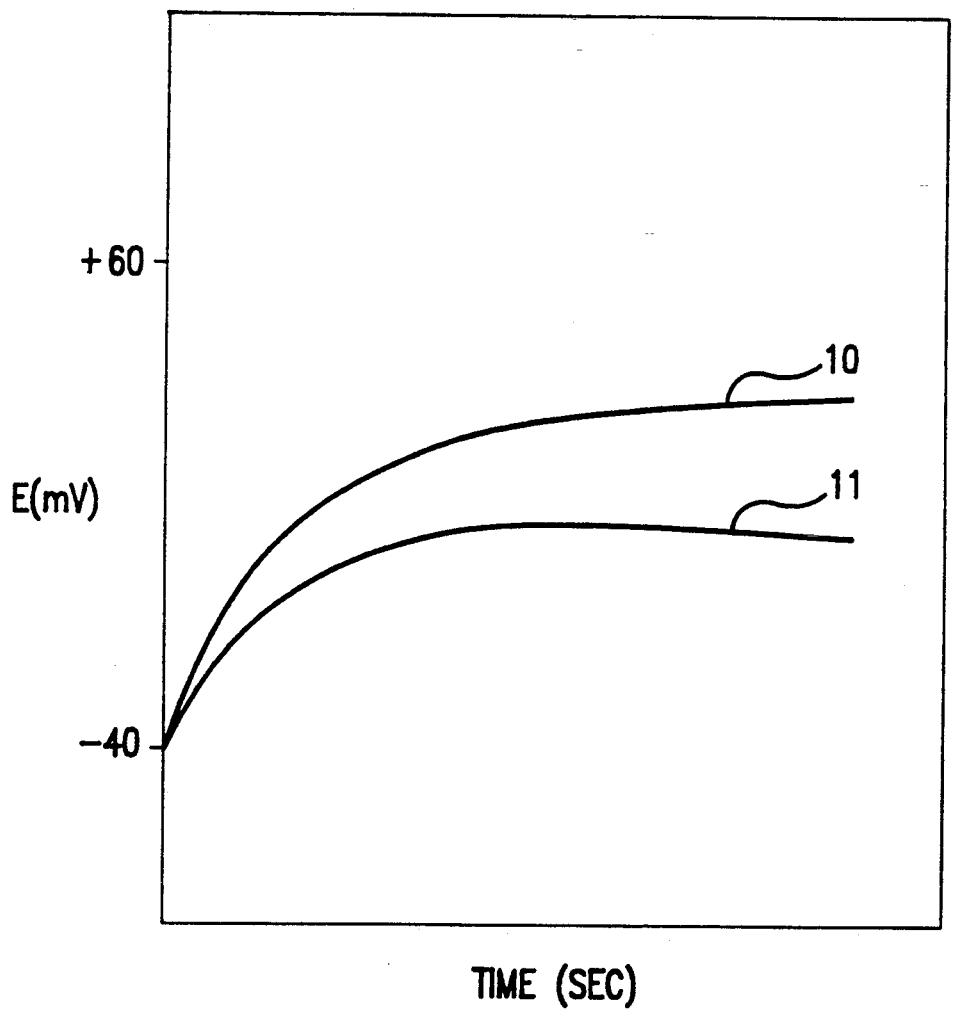
FIG. 2 is a potential-time diagram representing the equilibrating step.

During the equilibration step, no current is applied to the electrodes and the disk electrode is allowed to adsorb brightener for a period of time normally ranging between 5 seconds to 20 minutes, or until the equilibration potential becomes stable (i.e. change in potential with time is minimal). FIG. 2 shows the change in potential versus time for both a high brightener level (10) and a low brightener level (11) over a period of 100 seconds. It is important that the brightener concentration remain unchanged during analysis, by having sufficient volume present, and that temperature and agitation are controlled throughout the equilibration process. For example, when using a 0.156 inch diameter disk, a minimum of 100 ml sample would be a sufficient volume. At the end of this equilibration step, the level of brightener may be correlated to the final value of the potential.

Figure 3:
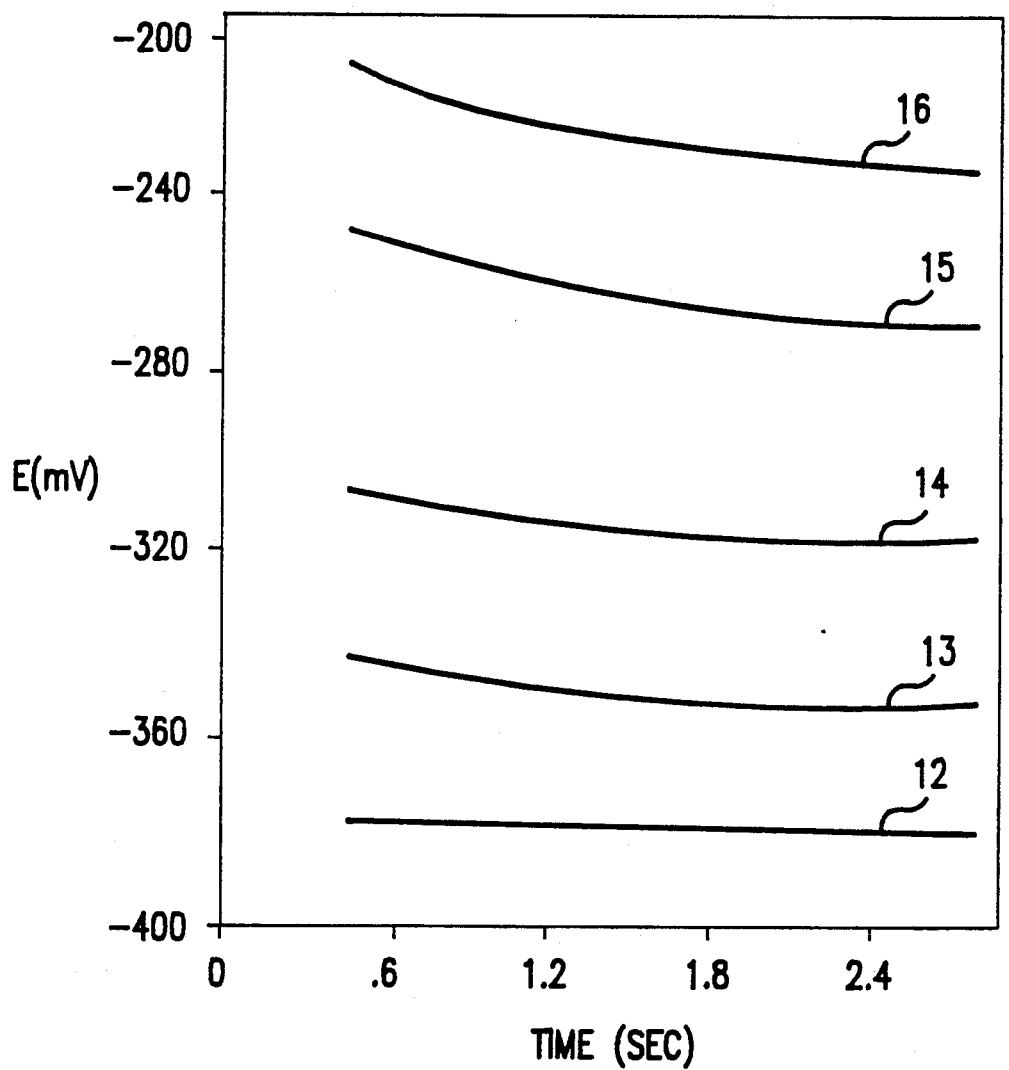
FIG. 3 is a potential-time plot of the initial plating potential for the metal plating step using various standard solutions.

In the next step, copper plating is initiated by plating at a current density from 1 to 100 ASF for 0.001 second to 60 seconds. During this time, copper ions are deposited on the electrode. These ions may be combined with or bound to leveler, brightener, chloride ions, water and/or wetting agents present in the bath. The initial potential reading, upon initiation of plating, is directly related to the brightener concentration. FIG. 3 shows the differences in the initial plating potential during a time period of 0.001 to 3 seconds, for standards containing varying concentrations of brightener at 100 ASF. Lines 12–16 correspond to concentrations of 0, 5, 10, 20 and 30 ppb of brightener, respectively. The following table correlates the initial potential to the concentration of brightener:

TABLE 1

| Concentration (ppb) | Potential (mV) |
|---|---|
| 0 | −378 |
| 5 | −345 |
| 10 | −310 |
| 20 | −260 |
| 30 | −220 |

As seen from the above data, sensitivity of the method allows for determinations of brightener concentration down to as little as 1 ppb.

Although the slope of the potential-time plot to be determined in the next step is a function of the ratio of brightener to leveler, the slopes may vary depending on the absolute concentration of brightener. Once the quantity of brightener is determined from the previous steps, it may be necessary to add additional brightener to the sample so that the amount of brightener more closely approximates the actual value of brightener in the standards. Once this is done, the ratio of brightener to leveler will more accurately reflect the absolute amount of leveler.

Figure 4:
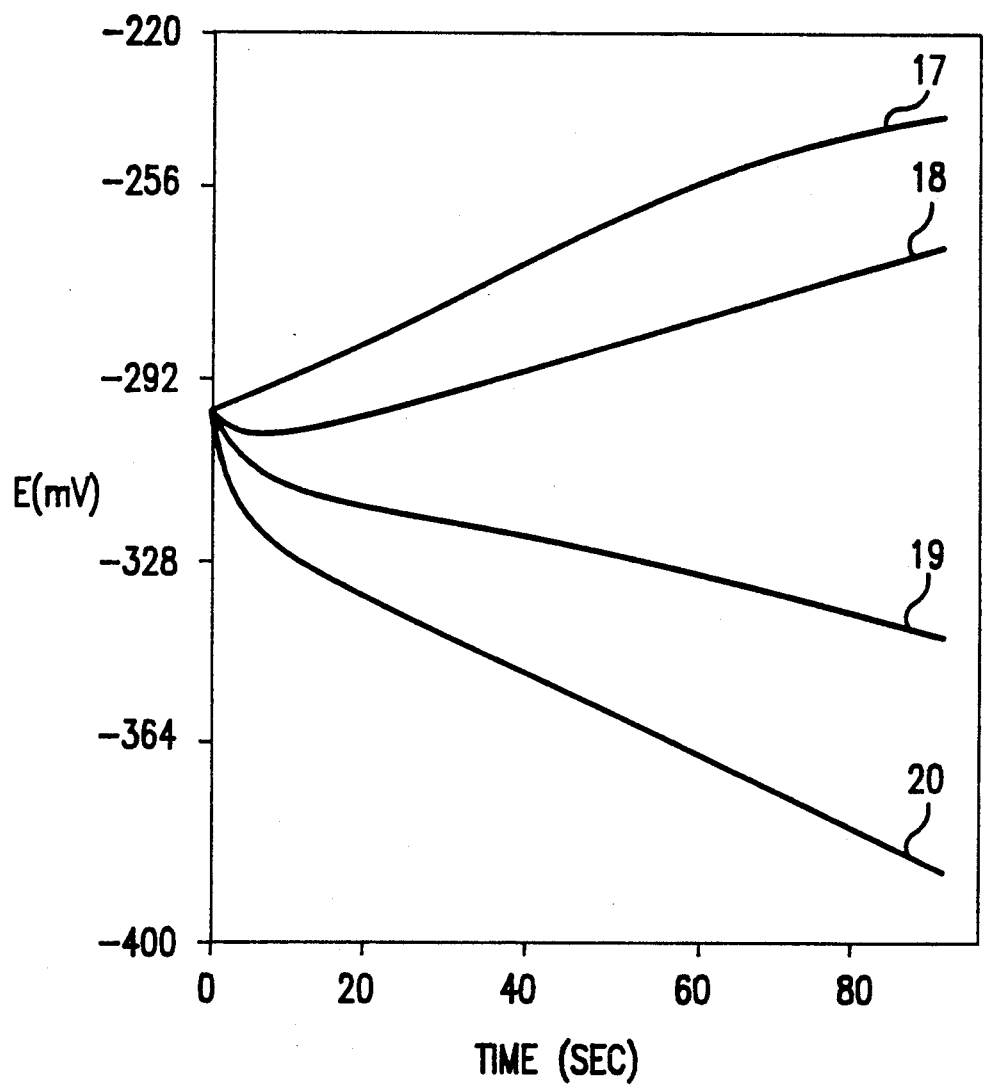
FIG. 4 is a potential-time diagram for the metal plating step for four standard solutions of known concentration.

As the plating process continues, changes in potential can also be correlated to the ratio of brightener to leveler. This step of continued plating may be at 1 to 100 ASF for a period of time ranging between 5 seconds to 10 minutes. FIG. 4 shows a typical plot of changes in voltage over time for various standard concentrations of leveler when the brightener is held constant at 90 ppb at 100 ASF. The slope of these lines can be correlated to the ratio of brightener to leveler in the bath, and is used to determine quantity of leveler present in the bath. Lines 17-20 correspond to leveler present in quantities of 0, 50, 100, and 150 ppb, respectively.

Figure 5:
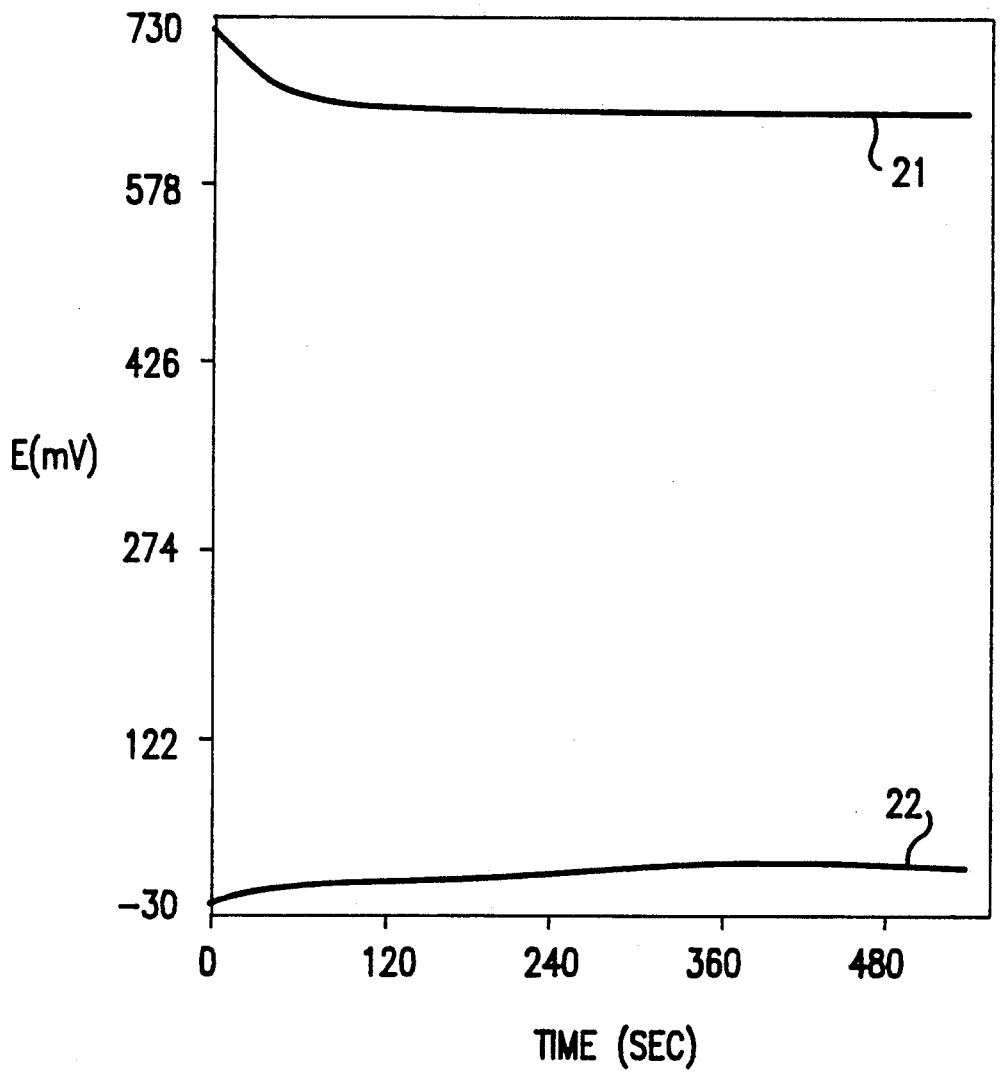
FIG. 5 is a potential-time diagram for the equilibrating step showing the difference in equilibration potentials between a platinum and copper working electrode.

In an alternate embodiment of the invention, an additional step of anodic pulse may be used before or after the equilibration step. This anodic pulse is carried out at +0.01 to +1.6 volts for a period of time ranging between 0.001 to 10 minutes. When the pulse step is used before the equilibration step, it serves to shorten the equilibration time; and when used after the equilibration step, it enhances potential driven adsorption of brighteners thereby increasing sensitivity. The advantages of using the pulse step are attributable to faster and greater adsorption of brightener. The potentials, used to enhanced adsorption, may also be related to the rest potential of various metals used as the working electrode during the equilibration step. FIG. 5 shows the differential adsorption of brightener on a platinum working electrode (21) compared to a copper working electrode (22). The equilibration potential for platinum is ~+650 mV and ~−20 mV for copper in this particular bath. This difference in equilibration potential accounts for the preferential anodic adsorption of brightener on a copper working electrode.

All of the embodiments of the present invention allow for improved sensitivity over prior art methods due to complete and specific saturation of brighteners and levelers on the surface of the metal disk. The following examples will serve to illustrate the operation of the invention but are not to be taken as limitations to the same.

EXAMPLE 1

Potential-time diagrams were formulated in accordance with the procedures of this invention utilizing a copper plating bath with the following composition:

| | |
|---|---|
| copper ions | 7.5 g |
| sulfuric acid | 300.0 g |
| chloride ion | 50.0 ppm |
| organic additives | as required |
| water | to 1 liter |

The bath was used at a temperature of 22° C. The organic additives used are any of those typically used in acid-copper plating baths such as those described above. The organic additive used was a proprietary brightener, leveler and carrier combination obtained from Shipley Company Inc., whose general formulas meet the criteria of containing the group $S-R_1-S$ for brightener and $N-R_1C-S$ for leveler, as defined above.

Figure 6:
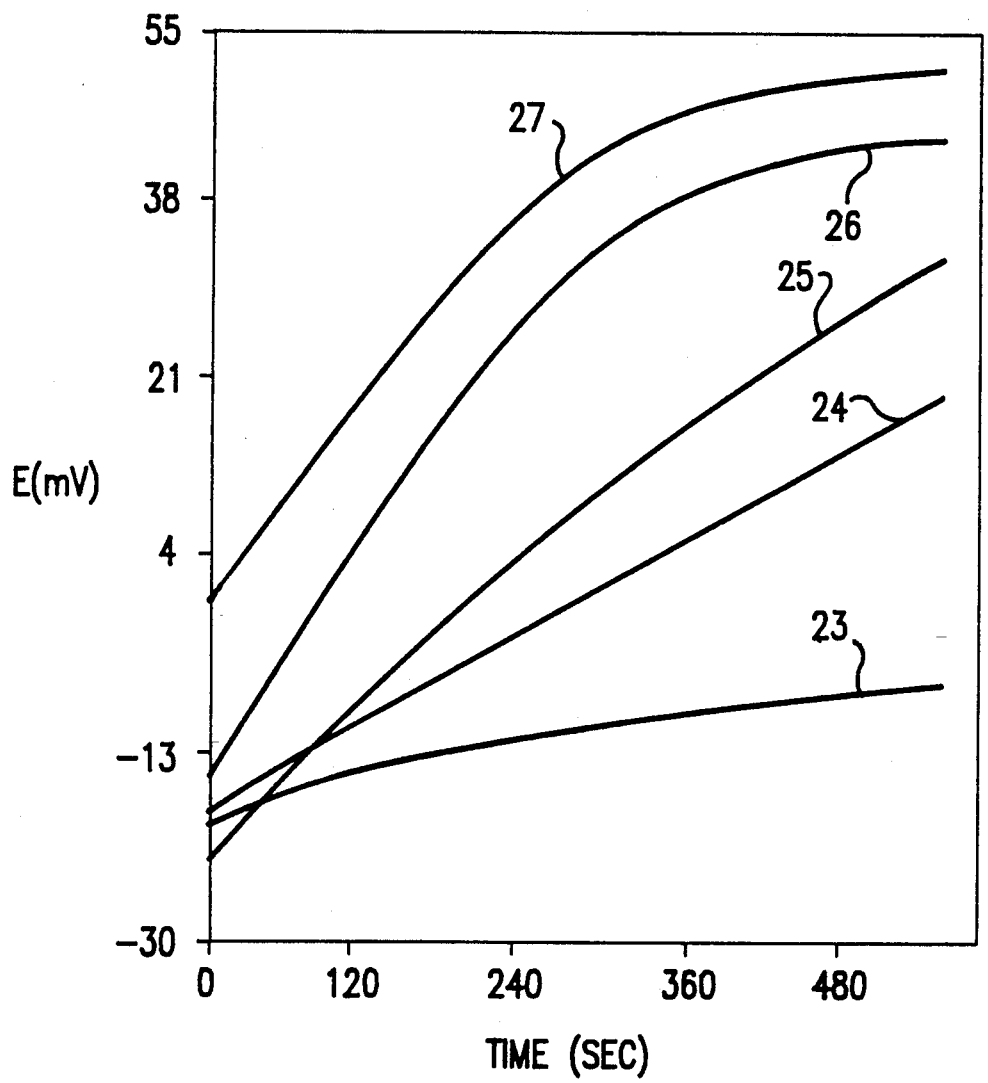
FIG. 6 is a potential-time diagram for the equilibrating step using five standards of known concentration.

FIG. 6 shows the changes in potential versus time during the equilibration step. Five standard bath solutions were used containing 0, 5, 10, 20 and 30 ppb of brightener, corresponding to lines 23-27, respectively.

Figure 7:
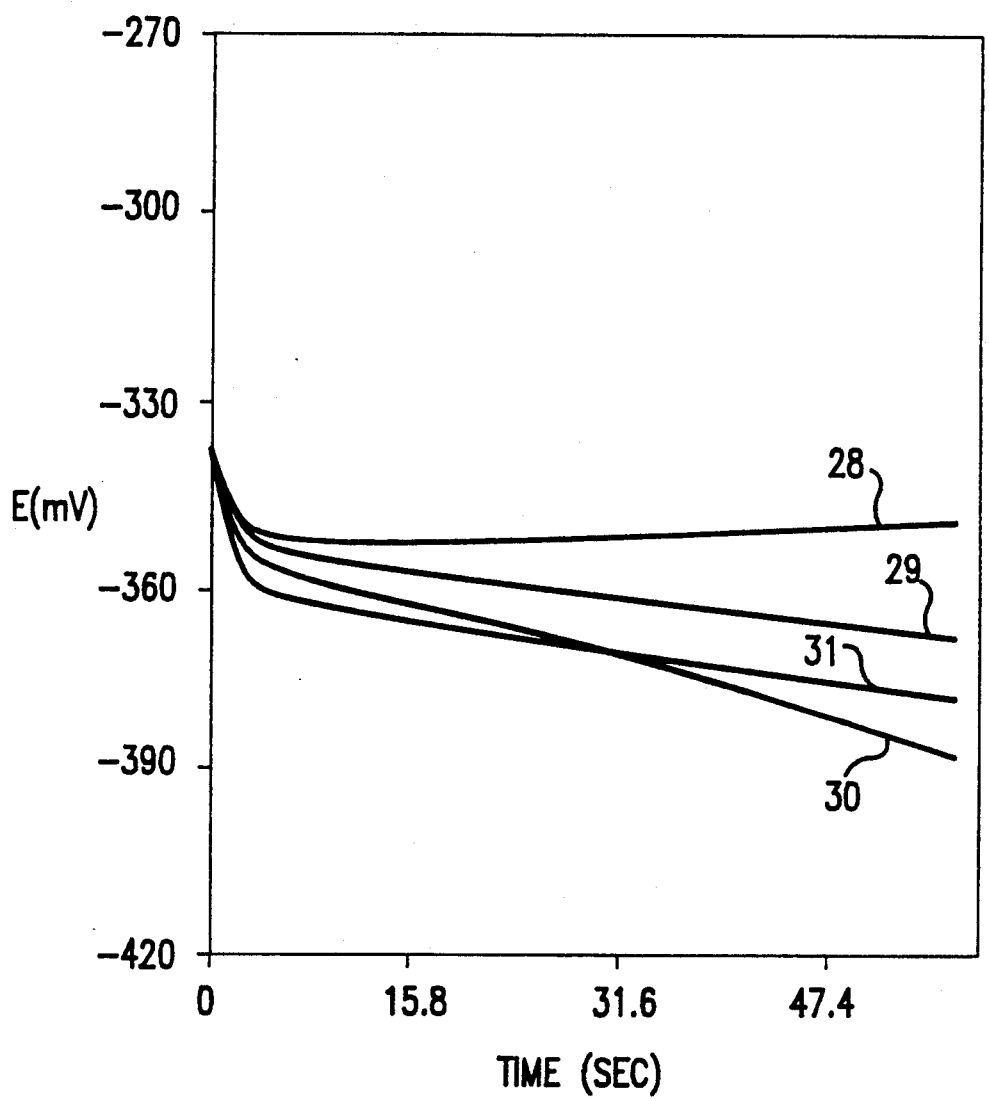
FIG. 7 is a potential-time diagram for the metal plating step for an actual bath and three (3) standard solutions of known concentration.

For FIG. 7, the concentration of organic brightener and leveler in an actual running bath was determined during the metal plating step by plotting the potential-time diagram and determining the slopes of those lines for three (3) standards. The first standard contained 30 ppb brightener/0 ppb leveler (28), the second standard contained 30 ppb brightener/30 ppb leveler (29), and the third standard contained 30 ppb brightener/60 ppb leveler (30). The slope of the line for the running bath (31) shows a ratio of brightener to leveler between the two standards of 30/30 and 30/60.

EXAMPLE 2

Potential-time diagrams were formulated in accordance with the procedures of this invention utilizing a copper plating bath with the following composition:

| | |
|---|---|
| copper ions | 7.5 g |
| sulfuric acid | 300.0 g |
| chloride ion | 50.0 ppm |
| organic additives | as required |
| water | to 1 liter |

Figure 8:
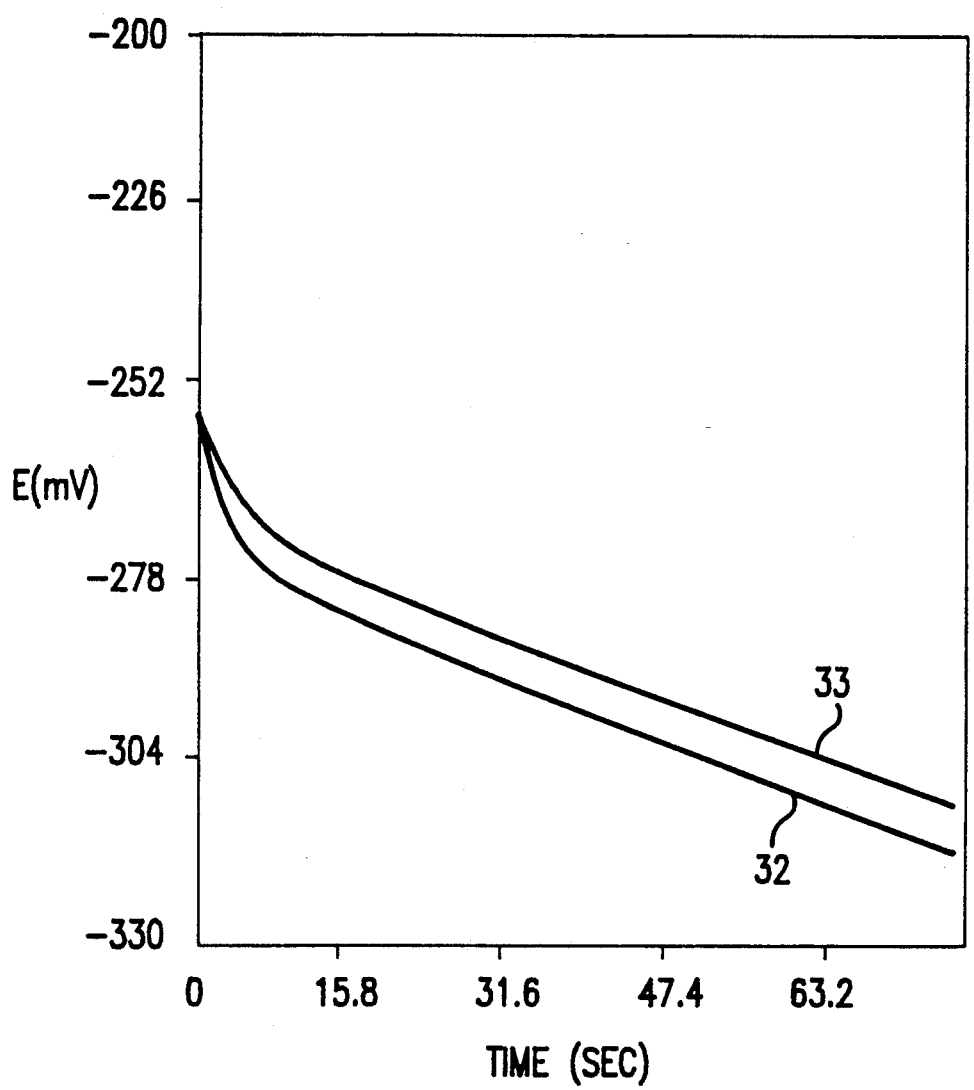
FIGS. 8 is a potential-time diagram for the metal plating step for a bath containing a constant amount of leveler and two different brighteners.

The bath was used at a temperature of 22° C. The organic additives used are any of those typically used in acid-copper plating baths such as those described above. In this particular example, two different brighteners (B1 and B2) were used in separate samples each containing the same leveler in accordance with the functionality requirements described above. The leveler amount was constant at 90 ppb and the brightener amount for both B1 (32) and B2 (33) was 90 ppb as shown in the potential-time plots during the metal plating step, FIG. 8. The two different lines indicate that the method may be applied to samples containing different brighteners as long as the functionality group described above is present in the brighteners.

EXAMPLE 3

Potential-time diagrams were formulated in accordance with the procedures of this invention utilizing a copper plating bath with the following composition:

| | |
|---|---|
| copper ions | 7.5 g |
| sulfuric acid | 300.0 g |
| chloride ion | 50.0 ppm |
| organic additives | as required |
| water | to 1 liter |

Figure 9:
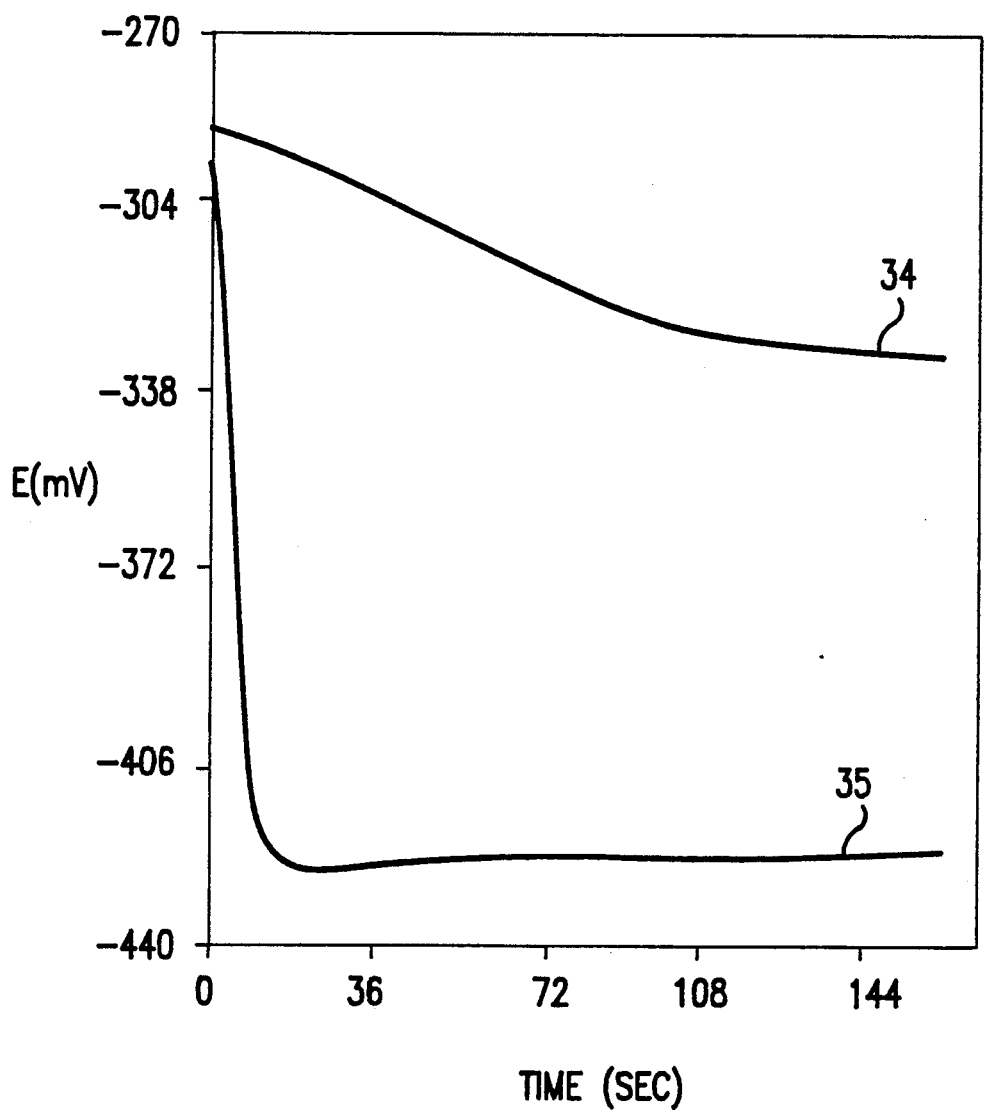
FIG. 9 is a potential-time diagram for the metal plating step for a bath containing a constant amount of brightener and two different levelers.

The bath was used at a temperature of 22° C. The organic additives used are any of those typically used in acid-copper plating baths such as those described above. In this particular example, two different levelers (L1 and L2) were used in separate samples each containing the same brightener in accordance with the functionality requirements as described above. The brightener amount was 90 ppb, while the leveler amount for both L1 (34) and L2 (35) was 90 ppb, as shown in the potential-time plot recorded during the metal plating step, FIG. 9. Again, the method may be applied to samples containing different levelers as long as the functionality group described above is present in the levelers.

What is claimed is:

1. A method for determining the quantity of brightener and leveler in a metal plating bath comprising the steps of:
   a. obtaining a plurality of plating baths where each bath has a known and different quantity of said brightener and leveler, but where the quantity of each in each bath differs from the quantity in the other baths;
   b. for each bath, providing a counter electrode, a cleaned working electrode and a reference electrode immersed in said bath, and carrying out a predetermined sequence of steps comprising:
      i. equilibrating said working electrode without energy input to adsorb brightener for a time until the change in energy output with time is minimal and measuring said energy output;
      ii. plating metal ions on said working electrode with energy input for a time sufficient to measure initial plating energy output; and
      iii. continuing to plate metal ions for a time sufficient to measure the change in energy output with time;
   c. for each bath, correlating the quantity of brightener with the energy output value obtained in step i;
   d. for each bath, correlating the quantity of brightener with the initial energy output value obtained in step ii;
   e. for each bath, correlating the ratio of brightener to leveler with the change in energy output with time value obtained in step iii;
   f. obtaining a plating bath having an unknown quantity of brightener and leveler, placing said electrodes in said bath and performing said predetermined sequence of steps; and
   g. choosing from said correlations in steps c, d and e, a quantity of brightener and the ratio of brightener to leveler which corresponds to said energy outputs recorded for said bath with the unknown quantity of brightener and leveler.

2. The method of claim 1 where said brightener contains the group $S-R_1-S$, where $R_1$ is alkyl or aryl.

3. The method of claim 1 where said leveler contains the group $N-R_1S$, where $R_1$ is alkyl or aryl.

4. The method of claim 1 wherein said metal plating bath is selected from the group consisting of copper, nickel, chromium, zinc, tin, gold, silver, lead, cadmium and solder baths.

5. The method of claim 1 wherein said metal plating bath is a copper bath.

6. The method of claim 1 wherein said working electrode comprises a metal disk.

7. The method of claim 1 wherein said cleaned working electrode is provided by a cleaning step for said electrode performed galvanostatically at 80 ASF until voltage reaches 1.6 volts.

8. The method of claim 1 wherein said cleaned working electrode is provided by a cleaning step for said electrode performed by rinsing with nitric acid followed by rinsing with deionized water.

9. The method of claim 1 wherein said energy input is potential and said energy output is current density.

10. The method of claim 1 wherein said energy input is current and said energy output is potential.

11. The method of claim 1 wherein said predetermined sequence of steps further comprises the step of initially plating a thin layer of metal on said working electrode prior to said equilibrating step.

12. The method of claim 11 wherein said thin layer of metal is applied at a current density of 1 to 100 ASF for a period of time ranging between 10 to 300 seconds.

13. The method of claim 1 wherein said predetermined sequence of steps further includes a step of applying an anodic voltage to the working electrode for a period of time ranging between 0.001 to 10 minutes prior to the step of equilibrating said working electrode.

14. The method of claim 1 wherein said step ii is carried out at 1 to 100 ASF for a period of time ranging between 0.001 second to 60 seconds.

15. The method of claim 1 wherein said step iii is carried out at 1 to 100 ASF for a period of time ranging between 5 seconds to 10 minutes.

16. A method for determining the quantity of one or more brighteners in a metal plating bath comprising the steps of:
   a. obtaining a plurality of plating baths, each having a known quantity of said brightener, but where the quantity of brightener in each bath differs from the quantity in the other baths;
   b. for each bath, providing a counter electrode, a cleaned working electrode and a reference electrode immersed in said bath, and equilibrating said working electrode without energy input to adsorb brightener for a time ranging between five seconds and twenty minutes until the change in potential of the working electrode with time is minimal, and measuring the value of said potential;
   c. for each bath, correlating the quantity of brightener with the value of potential obtained in step b;
   d. obtaining a plating bath having an unknown quantity of brightener, placing said electrodes in said bath and performing step b for said plating bath; and
   e. choosing from said correlations in step c a quantity of brightener which corresponds to the equilibrated working electrode potential for said bath with the unknown quantity of brightener.

17. The method of claim 16 where said brightener contains the groups $S-R_1-S$, where $R_1$ is alkyl or aryl.

18. The method of claim 16 where said metal plating bath of step d is a copper bath.

19. The method of claim 16 wherein an anodic voltage is applied to the working electrode for a period of time ranging between 0.001 to 10 minutes prior to the step of equilibrating said working electrode.

* * * * *